United States Patent [19]
> Lichon

[11] 4,188,724
[45] Feb. 19, 1980

[54] DENTAL IMPRESSION GUN
[76] Inventor: James F. Lichon, 1116 River Forest, Saginaw, Mich. 48603
[21] Appl. No.: 860,844
[22] Filed: Dec. 15, 1977
[51] Int. Cl.² .............................................. A61C 9/00
[52] U.S. Cl. ...................................... 433/90; 222/388
[58] Field of Search .................. 222/386, 388; 32/60, 32/17

[56] References Cited
U.S. PATENT DOCUMENTS

| | | | |
|---|---|---|---|
| 723,822 | 3/1903 | Buchanan | 32/60 |
| 990,895 | 5/1911 | Menger | 222/388 |
| 1,379,004 | 5/1921 | Edelmann | 222/388 |

*Primary Examiner*—Robert Peshock
*Attorney, Agent, or Firm*—Learman & McCulloch

[57] ABSTRACT

A side loading dental impression gun designed to accommodate rapid loading into the tubular barrel of the gun of a fast setting dental impression material. A syringe-like gun is formed with a relatively large door-like opening in the side of the barrel adjacent the discharge end of the gun to provide a relatively large opening through which a charge of a semi-fluent fast setting dental impression material can be introduced rapidly into the barrel. Various forms of door-latching or closing devices are disclosed for quickly conditioning the gun for dispensing the impression material with a minimum delay, thus preventing initial setting of the material within the gun.

5 Claims, 8 Drawing Figures

DENTAL IMPRESSION GUN

BACKGROUND OF THE INVENTION

One of the desired attributes of material employed by dentists for taking impressions of teeth is that the material, applied in a semi-fluent form, will set up rapidly to form the desired impression. Many materials suitable for this purpose are known. In the usual case, the impression material is mixed from two constituents which are kept separate from each other and mixed only immediately prior to use. The mixed material is applied to the area of which an impression is desired normally by a syringe having a relatively large nozzle which, for pusposes of description is conveniently termed a dental impression gun.

Impression materials presently in use are agar hydrocolloids, polysulfide rubbers, silicone rubbers, and alginate hydrocolloids. The latter material is considerably more viscous than the others.

After the material is mixed, it must be loaded into the gun and the gun prepared for operation. The usual technique it to remove the plunger, or the nozzle, from the gun, see U.S. Pat. No. 3,436,828, and introduce the mixed material into the gun barrel from the plunger end. The plunger is then reinserted into the barrel. While this operation is not complex, it must be recalled that the material normally is quite viscous and thus cannot be introduced into the barrel rapidly. Consequently, a substantial amount of time is consumed in transferring an adequate amount of the impression material from the mixing vessel to the relatively small opening defined by the diameter of the gun barrel. Because the material begins to set as soon as it is mixed, its properties of flowability rapidly deteriorate, thus increasing the possibility that the material when dispensed from the gun may be too stiff to fill all of the minor recesses and crevices in the region to which it is applied, thus resulting in an unsatisfactory impression.

This problem has been recognized in the prior art; see for example Hickes U.S. Pat. No. 2,825,134 in which a rather complex arrangement is provided so that mixing of the two constituents of the impression material can take place in the barrel of the gun.

The present invention is especially directed to various forms of dental impression guns designed to facilitate the rapid loading of an adequate quantity of a fast setting impression material into the barrel of the gun.

SUMMARY OF THE INVENTION

In accordance with the present invention, a dental impression gun is formed with a relatively large opening or passage through the side of the barrel at or closely adjacent the discharge end of the barrel and extending axially about one-half the length of the barrel. Various forms of closures for such opening are disclosed which enable the opening to be rapidly and positively closed once the charge of material is introduced so that the material may be dispensed from the gun with a minimum delay. The arrangements are such that the operating plunger of the gun need not be removed during the loading operation.

In two forms of the invention, the passage is closed by a hinged door. In one of these hinged door forms, the door is held closed by a snap type latch. In the other hinged door form of the invention, a sliding ring slidably mounted on the exterior of the barrel can be slipped swiftly into position to retain the door in its closed position. Both forms may employ an integral hinge arrangement.

In other forms of the invention, the door may take the form of a sliding cylindrical collar mounted on the exterior of the barrel which is simply advanced forwardly into overlying relationship with the opening in the barrel to provide the closure. Alternatively, an axially sliding door mounted on the barrel by a tongue and groove slideway may be employed.

Other objects and features of the invention will become apparent by reference to the following specification and to the drawings.

IN THE DRAWINGS

Figure 1:
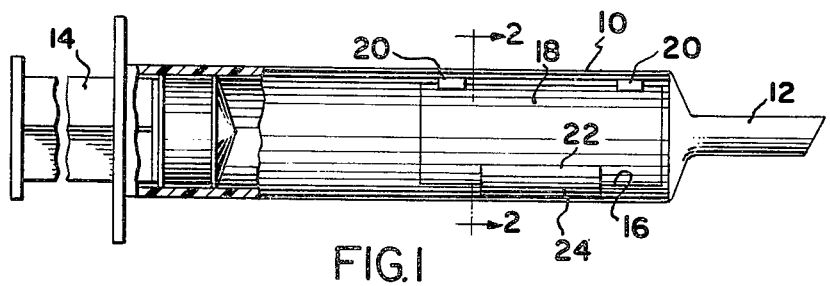
FIG. 1 is a side elevational view of one form of the invention.
Figure 2:
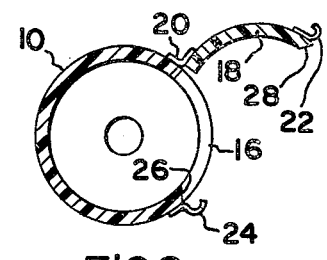
FIG. 2 is a detailed cross sectional view taken on the line 2—2 of FIG. 1 showing the door in its open position.

Referring first to FIGS. 1 and 2, one form of the invention is shown as being applied to a dental impression gun which includes a hollow cylindrical tube or barrel 10 having a relatively large bore nozzle 12 at one end and a plunger 14 of conventional construction slidably received within the interior of the barrel 10 and operable when manually depressed to expel material from the interior of the barrel 10 through nozzle 12. The barrel and nozzle may be formed from a relatively inexpensive plastic material inasmuch as the fast setting properties of the impression material dispensed by such guns makes cleaning of the gun for reuse impractical. See, for example, U.S. Pat. No. 3,436,828 referred to above. Alternatively, the barrel may be formed of stainless steel, for example, and the nozzle formed of a disposable plastic material.

In accordance with the present invention, a generally rectangular passage or opening 16 is cut in a side wall of barrel 10 and a door 18 is hingedly mounted, as by hinges 20, upon barrel 10 to function as a closure for opening 16. Because of the relatively high viscosity of the material which will be dispensed from the gun, precise sealing of door 18 within opening 16 is not highly essential. A simple snap type latch formed from resilient metal or plastic elements 22 and 24 fixedly mounted respectively on door 18 and barrel 10, as best seen in FIG. 2, is employed to latch the door in its closed position. Preferably, the mating edges of the opening and the door at 26,28 (FIG. 2) are beveled as illustrated to prevent the closed door from projecting into the interior of barrel 10. The dimensions of the opening 16 are chosen to be sufficiently large to accommodate a relatively rapid transfer of a charge of impression material into the interior of the barrel through the opened door.

During the introduction of material into the barrel through opening 16, plunger 14 is withdrawn to a position clear of the opening. When a sufficient volume of impression material has been introduced into the interior of the gun through the opening 16, door 18 is snapped shut and the device is ready to use in the conventional manner.

Figure 3:
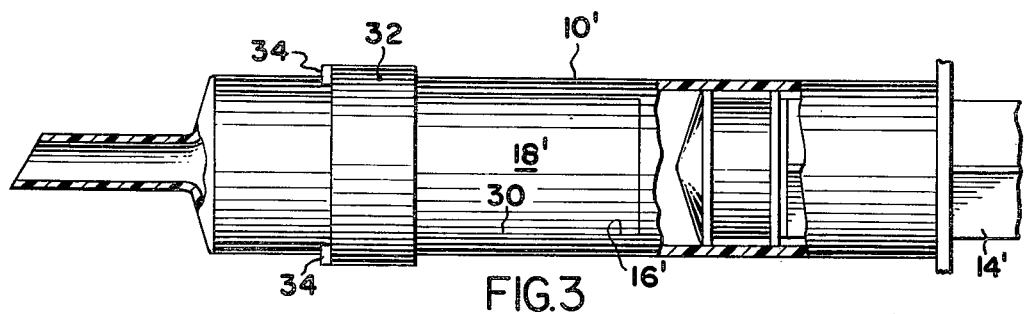
FIG. 3 is a side elevational view, with certain parts broken away, of another form of the invention.
Figure 4:
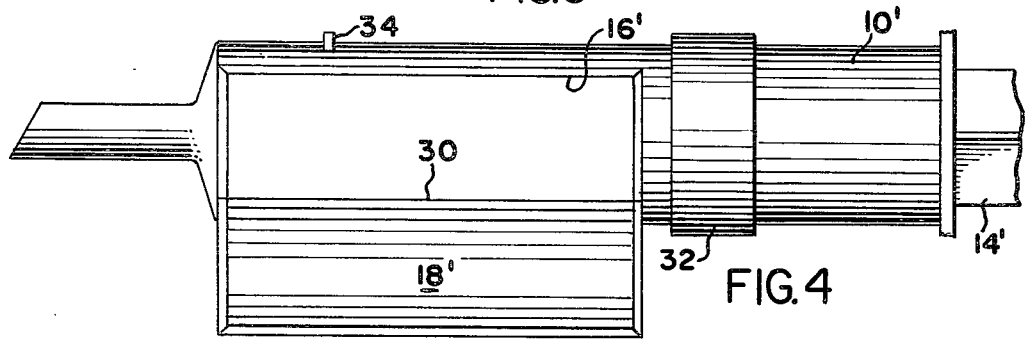
FIG. 4 is a detailed side elevational view of the device of FIG. 3 showing the door in its open position.

A modified form of the invention is shown in FIGS. 3 and 4. In this modified form of the invention, an elongate rectangular opening 16' is formed in the barrel 10' of a dental impression gun, the door 18' in this case being connected along edge 30 to barrel 10' by an integral hinge formed by a groove or a section of reduced wall thickness in barrel 10'. The remaining three edges of opening 16' and the corresponding edges of door 18' are beveled, as described above. In place of the spring type latch employed in the FIGS. 1 and 2 embodiment, the FIGS. 3 and 4 embodiment employs a sliding ring 32.

Ring 32 is slidably received upon barrel 10' and is retracted clear of the door, as illustrated in FIG. 4, when the door is to be opened for a loading operation. When the loading operation is complete, the door 18' is closed and ring 32 is slid forwardly on the closed door, as illustrated in FIG. 3, to hold the door in its closed position. One or more abutments 34 may be provided on the exterior of the barrel 10' to locate ring 32 in the door closing position, i.e., about midway of the axial length of the door.

Figure 5:
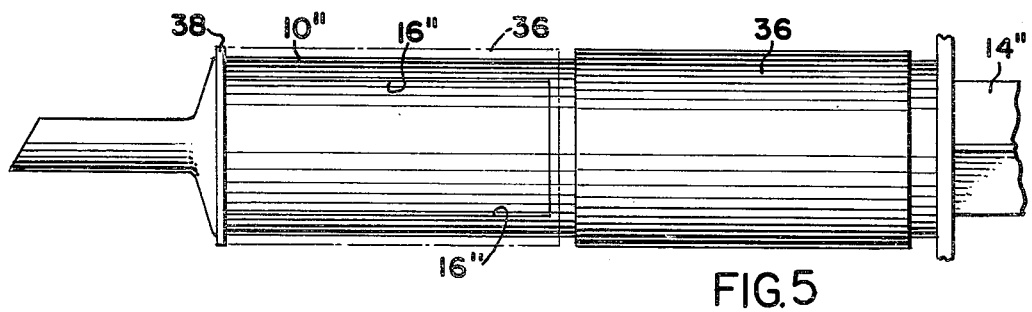
FIG. 5 is a side elevational view, with certain parts broken away, of still another form of the invention.

FIG. 5 illustrates a third embodiment of the invention wherein an opening 16" is cut through the wall of barrel 10" adjacent the nozzle end of the barrel. A cylindrical sleeve 36 of an axial length exceeding the axial length of opening 16", but preferably less than half the length of the barrel, is slidably received on the exterior of barrel 10" and a radial flange 38 is formed on the barrel 10" at the nozzle end of opening 16". To expose the opening 16" for loading of impression material into the interior of the barrel 10", sleeve 36 is retracted to the position shown in FIG. 5. When a chage of impression material has been loaded into the interior of the barrel 10", sleeve 36 is simply slid to the left from the position shown in FIG. 5 until it contacts flange 38, at which time opening 16" will be closed by sleeve 36.

Figure 6:
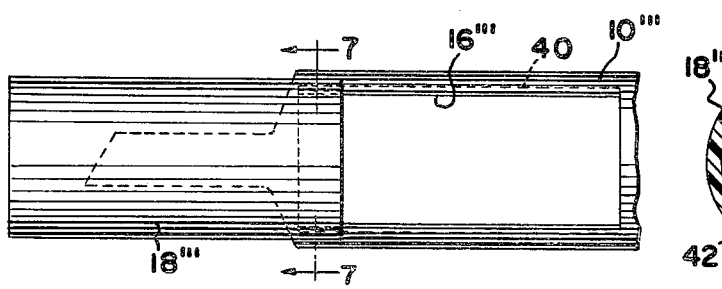
FIG. 6 is a side elevational view, with certain parts broken away, of still another form of the invention.
Figure 7:
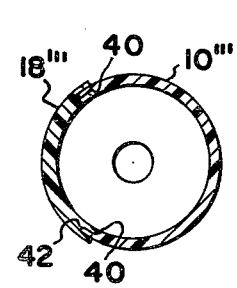
FIG. 7 is a cross sectional view of the device of FIG. 6, taken on the line 7—7 of FIG. 6.
Figure 8:
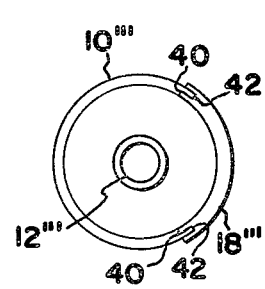
FIG. 8 is an end elevational view of the device of FIG. 6.

A fourth embodiment of the invention is illustrated in FIGS. 6-8. In this embodiment a generally rectangular opening 16''' is formed in the side wall of barrel 10''' adjacent the nozzle end of the barrel. The two axial edges of opening 16''' are formed with an undercut groove, as best seen at 40 in FIGS. 7 and 8 and a sliding door 18''' is formed with complimentary grooves 42 to slidably support door 18''' for sliding movement between the open position shown in FIG. 6 and a closed position in which opening 16''' is closed.

The four disclosed embodiments have in common the feature of providing a relatively large opening near the nozzle end of the barrel which will accommodate the rapid introduction of a fairly large volume of impression material into the interior of the barrel within a relatively short period of time. The material is introduced close to the nozzle and various forms of closures for the material receiving opening are provided which may be rapidly and simply closed and held in a closed position.

Although several embodiments of the invention have been described, it will be apparent to those skilled in the art that the disclosed embodiments may be modified. Therefore, the foregoing description is to be considered exemplary rather than limiting, and the true scope of the invention is that defined in the following claims.

I claim:

1. In a dental impression gun for applying a fast setting material, said gun comprising a hollow cylindrical tube having a nozzle at one end and a plunger slidably received in said tube for movement from a first position adjacent the opposite end of said tube toward said one end to force material from the interior of said tube outwardly through the nozzle; the improvement comprising a charging passage in a side wall of said tube, said passage terminating at one end adjacent said one end of said tube and at its other end short of said plunger when the latter is in said first position, said passage being of a size sufficient to enable the rapid loading of a charge of such material into the interior of said tube and wholly between said one end of the latter and said plunger; closure means for selectively opening and closing said passage; and retainer means slidably encircling said tube and being movable from a first position between said passage and said other end of said tube wherein said closure means is enabled to be opened, to a second position overlying said closure means, thereby enabling said closure means to be maintained in passage-closing position against force exerted on said closure means by said material while being discharged from said nozzle by said plunger.

2. The invention defined in claim 1 wherein said closure means comprises a cover member, and hinge means hingedly connecting said cover member along one side edge thereof to said tube for movement to and from a closed position seated in said passage.

3. The invention defined in claim 2 wherein said hinge means is substantially flush with said wall of said tube thereby enabling said retainer to be moved between said first and second positions.

4. The invention defined in claim 2 further comprising a ridge projecting outwardly from said tube engageable with said retainer means to locate the latter approximately midway of the axial length of said cover member when said cover member is in its passage-closing position.

5. In a dental impression gun for applying a fast setting material, said gun comprising a hollow cylindrical tube having a nozzle at one end and a plunger slidably received in said tube for movement from a first position adjacent the opposite end of said tube toward said one end to force material from the interior of said tube outwardly through the nozzle; the improvement comprising a charging passage in a side wall of said tube, said passage terminating at one end adjacent said one end of said tube and at its other end short of said plunger when the latter is in said first position, said passage being of a size sufficient to enable the rapid loading of a charge of such material into the interior of said tube and wholly between said one end of the latter and said plunger; and closure means for selectively opening and closing said passage, said closure means comprising a sleeve slidably mounted on said tube and having an axial length greater than that of said passage so as to be capable of wholly overlying said passage, the axial length of said sleeve being so related to the corresponding dimension of said tube as to enable said sleeve to be slid to a position on said tube in which said passage is wholly exposed.

* * * * *